United States Patent [19]

Nedelec et al.

[11] 4,278,677

[45] Jul. 14, 1981

[54] TETRAHYDROPYRIDINYL INDOLES

[75] Inventors: Lucien Nedelec, Le Raincy; Jacques Guillaume, Sevran; Claude Dumont, Nogent-sur-Marne, all of France

[73] Assignee: Roussel Uclaf, Paris, France

[21] Appl. No.: 2,453

[22] Filed: Jan. 10, 1979

[30] Foreign Application Priority Data

Jan. 16, 1978 [FR] France ................... 78 01083

[51] Int. Cl.³ .............. A61K 31/445; C07D 401/04
[52] U.S. Cl. ......................................... 424/263; 546/273
[58] Field of Search ........................ 546/273; 424/263

[56] References Cited

U.S. PATENT DOCUMENTS

| | | | |
|---|---|---|---|
| 2,872,453 | 2/1959 | Jacob et al. | 546/273 X |
| 3,429,886 | 2/1969 | Beck et al. | 546/273 |
| 3,501,484 | 3/1970 | Schut et al. | 546/273 |
| 3,980,658 | 9/1976 | Possanza et al. | 424/263 |
| 3,993,764 | 11/1976 | Dumont et al. | 424/267 |
| 4,196,209 | 4/1980 | Dumont et al. | 424/263 |

FOREIGN PATENT DOCUMENTS 2362628   3/1978   France .

OTHER PUBLICATIONS

Freter, J. Org. Chem., vol. 40, No. 17, (1975) pp. 2527-2529.

*Primary Examiner*—Richard Raymond
*Attorney, Agent, or Firm*—Hammond & Littell, Weissenberger and Muserlian

[57] ABSTRACT

Novel tetrahydropyridinyl indoles of the formula

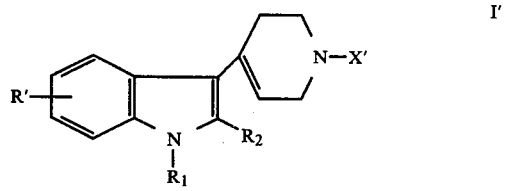

wherein R' is selected from the group consisting of hydrogen, halogen and alkoxy of 1 to 3 carbon atoms, $R_1$ and $R_2$ are individually selected from the group consisting of hydrogen and alkyl of 1 to 3 carbon atoms and X' is selected from the group consisting of alkyl of 1 to 6 carbon atoms, cycloalkyl of 4 to 7 carbon atoms, alkenyl and alkynyl of 2 to 5 carbon atoms and aralkyl of 7 to 12 carbon atoms with the proviso that when X' is methyl, at least one of R', $R_1$ and $R_2$ contain more than one carbon atom and when X' is benzyl, at least one of R', $R_1$ and $R_2$ must not be hydrogen and their non-toxic, pharmaceutically acceptable acid addition salts having antidepressive and neuroleptic properties as well as antiemetic properties.

39 Claims, No Drawings

TETRAHYDROPYRIDINYL INDOLES

STATE OF THE ART

Various related indoles are described in U.S. Pat. No. 3,993,764, French Pat. No. 2,227,873, Belgium Pat. No. 858,101 and J. Org. Chem., Vol 40, 17 (1975), p. 2527.

OBJECTS OF THE INVENTION

It is an object of the invention to provide the novel indoles of formula I' and their non-toxic, pharmaceutically acceptable acid addition salts and a novel process for their preparation.

It is another object of the invention to provide novel antidepressant and neuroleptic compositions and to provide a novel method of inducing antidepressant and neuroleptic activity in warm-blooded animals.

These and other objects and advantages of the invention will become obvious from the following detailed description.

THE INVENTION

The novel tetrahydropyridinyl indoles of the invention are comprised of compounds of the formula

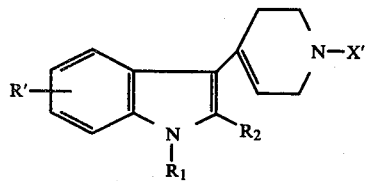

wherein R' is selected from the group consisting of hydrogen halogen and alkoxy of 1 to 3 carbon atoms, $R_1$ and $R_2$ are individually selected from the group consisting of hydrogen and alkyl of 1 to 3 carbon atoms and X' is selected from the group consisting of alkyl of 1 to 6 carbon atoms, cycloalkyl of 4 to 7 carbon atoms, alkenyl and alkynyl of 2 to 5 carbon atoms and aralkyl of 7 to 12 carbon atoms with the proviso that when X' is methyl, at least one of R', $R_1$ and $R_2$ contain more than one carbon atom and when X' is benzyl, at least one of R', $R_1$ and $R_2$ must not be hydrogen and their non-toxic, pharmaceutically acceptable acid addition salts.

A preferred group of compounds are those of the formula

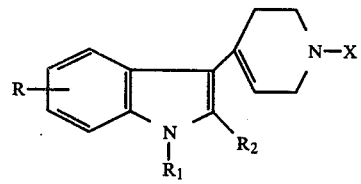

wherein R is selected from the group consisting of hydrogen and alkoxy of 1 to 3 carbon atoms, $R_1$ and $R_2$ have the above definition and X is alkyl of 1 to 6 carbon atoms with the proviso that when X is methyl, at least one of R, $R_1$ and $R_2$ contains more than one carbon atom and their non-toxic, pharmaceutically acceptable acid addition salts.

In the compounds of formulae I and I', R and R' are preferably in the 5- or 6-position of the indole. Examples of suitable alkoxy of 1 to 3 carbon atoms are methoxy, ethoxy and propoxy and of halogens are chlorine, bromine and fluorine. Examples of alkyl of 1 to 3 carbon atoms are methyl, ethyl and propyl and cycloalkyl of 4 to 7 carbon atoms are cyclopropylmethyl, cyclopentyl and cyclohexyl. Examples of alkenyl and alkynyl of 2 to 5 carbon atoms are vinyl, allyl, buten-2-yl, penten-2-yl and propargyl. Examples of aralkyl of 7 to 12 carbon atoms are benzyl and phenethyl and of alkyl of 1 to 6 carbon atoms are methyl, ethyl, propyl, isopropyl, butyl, isobutyl, pentyl and isopentyl.

Examples of suitable acids for the non-toxic, pharmaceutically acceptable acid addition salts are mineral acids such as hydrochloric acid, hydrobromic acid, hydroiodic acid, nitric acid, sulfuric acid and phosphoric acid and organic acids such as formic acid, acetic acid, benzoic acid, maleic acid, fumaric acid, succinic acid, tartaric acid, citric acid, glyoxylic acid, oxalic acid, aspartic acid, alkane sulfonic acids such as methane sulfonic acid and arylsulfonic acids such as benzene sulfonic acid.

Among the preferred compounds of formula I' are those wherein R' is halogen, those wherein $R_1$ and $R_2$ are hydrogen or methyl, those wherein X' is alkyl of 2 to 6 carbon atoms and especially those wherein R' is chlorine in the 5-position, $R_1$ and $R_2$ are hydrogen and X' is alkyl of 2 to 6 carbon atoms and their non-toxic, pharmaceutically acceptable acid addition salts.

Among the preferred compounds of formula I are those wherein R is hydrogen or methoxy, those wherein $R_1$ and $R_2$ are individually hydrogen or methyl and those wherein X is alkyl of 2 to 6 carbon atoms and especially those wherein R is hydrogen or 5-methoxy, $R_1$ and $R_2$ are hydrogen and X is alkyl of 2 to 6 carbon atoms and their non-toxic, pharmaceutically acceptable acid addition salts.

Specific preferred compounds are 3-(1-propyl-1,2,3,6-tetrahydropyridin-4-yl)-1H-indole hydrochloride, the neutral fumarate of 5-methoxy-3-(1-propyl-1,2,3,6-tetrahydropyridin-4-yl)-1H-indole, 3-(1-pentyl-1,2,3,6-tetrahydropyridin-4-yl)-1H-indole hydrochloride and 5-chloro-3-(1-propyl-1,2,3,6-tetrahydropyridin-4-yl)-1H-indole hydrochloride.

The novel process of the invention for the preparation of the compounds of formula I' comprises reacting a compound of the formula

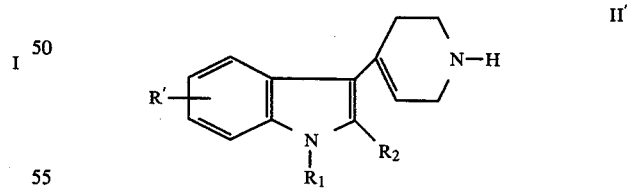

wherein R', $R_1$ and $R_2$ have the above definitions with an alkyl halide of the formula Hal—X'                       III' wherein X' has the above definition and Hal is chlorine, bromine or iodine to obtain the corresponding compound of formula I' which, if desired, may be reacted with an acid to form the acid addition salt.

The process for the preparation of compounds of formula I comprises reacting a compound of the formula

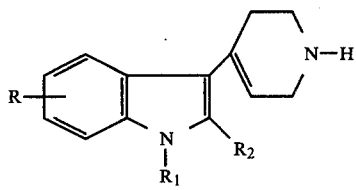

wherein R, $R_1$ and $R_2$ have the above definitions with an alkyl halide of the formula Hal—X       III wherein Hal and X have the above definitions to form the corresponding compound of formula I which, if desired, may be reacted with an acid to form the corresponding salt.

In a preferred mode of the processes, the condensation is effected in an organic solvent such as acetone, in the presence of silver oxide or sodium carbonate but may also be effected in triethylamine in the presence of hexametapol. The acid addition salts may be formed by reacting substantially stoichiometric amounts of the base and the acid.

The novel compositions of the invention having antidepressive, antiemetic and neuroleptic activity are comprised of an effective amount of at least one compound of formula I' and its non-toxic, pharmaceutically acceptable acid addition salts and an inert pharmaceutical carrier. The compositions may be in the form of tablets, dragees, gelules, granules, capsules, suppositories or injectable solutions or suspensions.

Examples of suitable carriers or excipients are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersants and emulsifiers.

The compositions are useful for the treatment of pyschic troubles, behavior problems, character problems, in the treatment of vomitting and nausea of all origins.

Particularly preferred are the compositions containing compounds of formula I' are those wherein R' is halogen, those wherein $R_1$ and $R_2$ are hydrogen or methyl, those wherein X' is alkyl of 2 to 6 carbon atoms and especially those wherein R' is chlorine in the 5-position, $R_1$ and $R_2$ are hydrogen and X' is alkyl of 2 to 6 carbon atoms and their non-toxic, pharmaceutically acceptable acid addition salts.

Among the preferred compositions are those containing compounds of formula I wherein R is hydrogen or methoxy, those wherein $R_1$ and $R_2$ are individually hydrogen or methyl and those wherein X is alkyl of 2 to 6 carbon atoms and especially those wherein R is hydrogen or 5-methoxy, $R_1$ and $R_2$ are hydrogen and X is alkyl of 2 to 6 carbon atoms and their non-toxic, pharmaceutically acceptable acid addition salts.

Specific preferred compositions are those wherein the active compound is selected from the group consisting of 3-(1-propyl-1,2,3,6-tetrahydropyridin-4-yl)-1H-indole hydrochloride, the neutral fumarate of 5-methoxy-3-(1-propyl-1,2,3,6-tetrahydropyridin-4-yl)-1H-indole, 3-(1-pentyl-1,2,3,6-tetrahydropyridin-4-yl)-1H-indole hydrochloride and 5-chloro-3-(1-propyl-1,2,3,6-tetrahydropyridin-4-yl)-1H-indole hydrochloride.

The novel method of the invention for the treatment of psychic disorders in warm-blooded animals, including humans, comprises administering to warm-blooded animals an amount of at least one compound of formula I or I' and its non-toxic, pharmaceutically acceptable acid addition salts sufficient to relieve psychic disorders. The compounds may be administered orally, rectally or parenterally, preferably orally. The usual useful dose is 0.1 to 4 mg/kg when administered orally.

The compounds of formulae II or II' which are not know may be prepared by reacting a compound of the formula

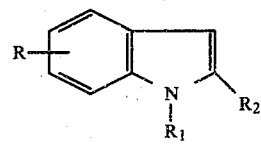

or

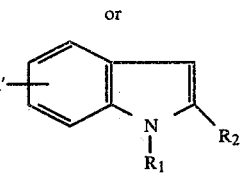

wherein R, R', $R_1$ and $R_2$ have the above definitions with 4-piperidone hydrochloride in acetic acid in the optional presence of a strong acid or a basic medium such as methanolic potassium hydroxide. An acid media is preferred when $R_1$ is alkyl.

The preparation of certain of the derivatives figure in French patent application No. 2,362,628 and its first certificate of addition.

In the following examples there are described several preferred embodiments to illustrate the invention. However, it should be understood that the invention is not intended to be limited to the specific embodiments.

EXAMPLE 1

Neutral fumarate of 5-methoxy-3-(1-propyl-1,2,3,6-tetrahydropyridin-4-yl)-1H-indole

STEP A:

5-methoxy-3-(1,2,3,6-tetrahydropyridin-4-yl)-1H-indole 44 g of the hydrochloride of 4-piperidone monohydrate were added at 100° C. to a solution of 12.6 g of 5-methoxy-indole in 240 ml of acetic acid and the mixture was held at 100° C. for 30 minutes and was then cooled and poured into ice water containing 400 ml of concentrated ammonium hydroxide solution. The mixture was extracted with ethyl acetate and the organic phase was washed with aqueous sodium chloride solution, was dried over magnesium sulfate and was evaporated to dryness to obtain 20 g of raw product. The latter was chromatographed over silica gel and elution with a 7-2-1 chloroform-methanol-triethylamine mixture yielded 5.26 g of 5-methoxy-3-(1,2,3,6-tetrahydropyridin-4-yl)-1H-indole in the form of a resin.

STEP B:
5-methoxy-3-(1-propyl-1,2,3,6-tetrahydropyridin-4-yl)-1H-indole

A suspension of 6 g of the product of Step A, 60 ml of triethylamine, 6 ml of hexamethylphosphotriamide and 3 ml of propyl iodide was heated at 80° C. for 30 minutes and then 0.5 ml of propyl iodide were added thereto. The mixture was held at 80° C. for another 30 minutes and was then cooled and 10 ml of water and 20 ml of methanol were added thereto. The mixture was extracted with methylene chloride and the decanted organic phase containing the amine fraction was extracted with N hydrochloric acid. The aqueous acid phase was made alkaline by addition of sodium carbonate and was extracted with methylene chloride. The organic phase was washed, dried and evaporated to dryness to obtain 6 g of product which was dissolved in 5 ml of methanol. 15 ml of ethyl acetate were added to the solution and the mixture was filtered. The recovered crystals were rinsed with ethyl acetate and dried to obtain 5-methoxy-3-(1-propyl-1,2,3,6-tetrahydropyridin-4-yl)-1H-indole melting at 164° C.

STEP C: Neutral fumarate of 5-methoxy-3-(1-propyl-1,2,3,6-tetrahydropyridin-4-yl)-1H-indole A solution of 3.1 g of the product of Step B in 15 ml of methanol was poured into a solution of 0.68 g of fumaric acid in 15 ml of methanol and the methanol was evaporated under reduced pressure. 20 ml of isopropanol were added to the residue and the mixture was stirred for 30 minutes at room temperature and then 30 minutes at 0° C. The mixture was filtered and the recovered product was rinsed with isopropanol and dried to obtain 3.5 g of raw product which was crystallized to obtain 2.13 g of the neutral fumarate of 5-methoxy-3-(1-propyl-1,2,3,6-tetrahydropyridin-4-yl)-1H-indole melting at 200° C.

Analysis: $C_{38}H_{48}N_4O_6$; molecular weight=656.836. Calculated: %C 69.49, %H 7.37, %N 8.53. Found: %C 69.7, %H 7.7, %N 8.6.

EXAMPLE 2

3-(1-propyl-1,2,3,6-tetrahydropyridin-4-yl)-1H-indole hydrochloride

STEP A: 3-(1,2,3,6-tetrahydropyridin-4-yl)-1H-indole 50 ml of aqueous N phosphoric acid and 39.3 g of the hydrochloride of 4-piperidone monohydrate were added under a nitrogen atmosphere to a stirred solution of 10 g of indole in 200 ml of acetic acid heated to 95°–100° C. and the mixture was held at 100° C. for one hour and was then cooled. The mixture was poured into 350 ml of concentrated ammonium hydroxide containing ice and the mixture was extracted with ethyl acetate. The organic extract was washed with water, with aqueous sodium chloride solution and was dried over magnesium sulfate and evaporated to dryness to obtain 14.7 g of raw product. The latter was empasted with 75 ml of methanol under nitrogen and the mixture was vacuum filtered. The recovered product was rinsed with methanol and ether to obtain 1.42 g of 3-(1,2,3,6-tetrahydropyridin-4-yl)-1H-indole melting at 185°–186° C. The mother liquors were evaporated and the residue was chromatographed over silica gel. Elution with a 6-3-1 chloroform-methanol-triethylamine mixture yielded 4.55 g of product with a Rf=0.15 and the latter was empasted with ether to obtain 4.295 g of the desired product for a total yield of 5.715 g. The latter was crystallized from hot and cold isopropanol to obtain 3.56 g of the product melting at 190°–191° C.

STEP B:
3-(1-propyl-1,2,3,6-tetrahydropyridin-4-yl)-1H-indole hydrochloride 3.15 g of silver oxide and 2.25 ml of isopropyl iodide were added to a solution of 4.5 g of 3-(1,2,3,6-tetrahydropyridin-4-yl)-1H-indole in 90 ml of acetone and the mixture was heated at 50° C. for 3 hours and was then cooled. The mixture was filtered and the filtrate was distilled to dryness under reduced pressure. The residue was chromatographed over silica gel and was eluted with a 6-3-1 chloroform-acetone-triethylamine mixture. The fractions were distilled to dryness and the residue was dissoved in 200 ml of refluxing ethyl acetate. The mixture was filtered and the filtrate was concentrated to 150 ml and cooled to 20° C. Crystallization was induced and the mixture was iced overnight and vacuum filtered. The recovered product was washed with ethyl acetate and dried to obtain 3.9 g of 3-(1-propyl-1,2,3,6-tetrahydropyridin-4-yl)-1H-indole melting at 210° C.

The said product was dissolved in 250 ml of refluxing isopropanol and an isopropanol solution of gaseous hydrogen chloride was added thereto dropwise until the pH was acid. The mixture was iced for 2 hours and was vacuum filtered. The recovered product was rinsed with isopropanol and dried to obtain 4.15 g of raw product which was crystallized to obtain 3.55 g of the hydrochloride of 3-(1-propyl-1,2,3,6-tetrahydropyridin-4-yl)-1H-indole melting at 230°~232° C.

Analysis: $C_{16}H_{20}N_2.HCl$; molecular weight=276.821 Calculated: %C 69.42, %H 7.65, %N 10.12, %Cl 12.81. Found: %C 69.5, %H 7.7, %N 9.9, %Cl 12.8.

EXAMPLE 3

3-(1-pentyl-1,2,3,6-tetrahydropyridin-4-yl)-1H-indole hydrochloride 5.18 g of silver oxide and then 20 ml of pentyl iodide were added to a solution of 10 g of 3-(1,2,3,6-tetrahydropyridin-4yl)-1H-indole in 100 ml of acetone and after stirring the mixture for 4 hours at room temperature, another 2.5 ml of pentyl iodide were added thereto. The mixture was stirred for one hour and was filtered and the filter was rinsed with a 1-1 methylene chloride-methanol mixture. The filtrate was evaporated to dryness under reduced pressure at 40° C. and the residue was chromatographed over silica gel. Elution was effected with a 7-2-1 chloroform-methanol-triethylamine mixture and the residue from evaporation of the solvents was extracted with 250 ml of refluxing ethanol. The organic extract was filtered and crystallization of the filtrate was effected at 0° to 5° C. to obtain 7.9 g of 3-(1-pentyl-1,2,3,6-tetrahydropyridin-4-yl)-1H-indole melting at about 180° C.

A suspension of the said product in 100 ml of absolute ethanol was admixed at 0° to 5° C. with 30 ml of an ethanolic solution saturated with gaseous hydrogen chloride and the mixture was stirred for one hour and was filtered. The recovered product was washed with ether and was dried under reduced pressure at 40° to 50° C. to obtain 8.45 g of the hydrochloride of 3-(1-pentyl-1,2,3,6-tetrahydropyridin-4-yl)-1H-indole in the form of a yellow product melting at 210° C. and then 240° C.

Analysis: $C_{18}H_{25}N_2Cl$; molecular weight=304.866
Calculated: %C 70.9, %H 8.3, %N 9.2, %Cl 11.6.
Found: %C 70.7, %H 8.3, %N 9.2, %Cl 11.6.

EXAMPLE 4

3-(1-ethyl-1,2,3,6-tetrahydropyridin-4-yl)-1H-indole hydrochloride

A mixture of 9.91 g of 3-(1,2,3,6-tetrahydropyridin-4-yl)-1H-indole, 10.6 g of sodium carbonate, 150 ml of dimethylformamide and 4.5 g of ethyl bromide was stirred under an inert atmosphere at 30°–35° C. for 5 hours and was then poured into 1.5 liters of water which caused precipitation. The mixture was stirred for one hour and filtered and the filter was rinsed with water. The recovered product was dried overnight in an oven at 70° C. under reduced pressure in the presence of dehydrating agent to obtain 8.95 g of raw product melting at 205° C. The product was dissolved in 400 ml of refluxing ethyl acetate and the mixture was filtered hot. The filtrate was concentrated to 250 ml and crystallization was effected for one hour. The mixture was filtered and the recovered product was rinsed with ethyl acetate to obtain 6.28 g of 3-(1-ethyl-1,2,3,6-tetrahydropyridin-4-yl)-1H-indole in the form of yellow crystals melting at 205° C. Concentration of the mother liquors yielded another 1.76 g of product after crystallization for a total yield of 8.04 g.

A suspension of the said product in 80 ml of iced methanol was admixed with an ethanolic solution of gaseous hydrogen chloride until the pH was acidic and precipitation was effected by allowing the mixture to stand for 30 hours. The mixture was filtered and the product was rinsed with ethanol and was dried under pressure at room temperature to obtain 8.67 g of raw product which was crystallized twice from ethanol to obtain 6.21 g of the hydrochloride of the product melting at 232°–233° C.

Analysis: $C_{15}H_{19}ClN_2$; molecular weight=262.789
Calculated: %C 69.42, %H 7.65, %N 10.12, %Cl 12.81.
Found: %C 69.5, %H 7.7, %N 9.9, %Cl 12.8.

EXAMPLE 5

3-(1-isopropyl-1,2,3,6-tetrahydropyridin-4-yl)-1H-indole hydrochloride

A mixture of 5 g of 3-(1,2,3,6-tetrahydropyridin-4-yl)-1H-indole, 50 ml of dimethylformamide, 5.25 g of sodium carbonate and 2.7 ml of 2-iodopropane were stirred under an inert atmosphere and the mixture was then added dropwise over 20 hours to 400 ml of water. The mixture was stirred for 30 minutes, was allowed to crystallize and was then vacuum filtered. The recovered product was washed and dried at 50° C. under reduced pressure to obtain 5.8 g of 3-(1-isopropyl-1,2,3,6-tetrahydropyridin-4-yl)-1H-indole melting at 178° C.

The said product was dissolved in 150 ml of hot isopropanol and a propanol solution of gaseous hydrogen chloride was added thereto dropwise until the pH was acidic. The mixture was allowed to crystallize and stood overnight in ice and was then vacuum filtered. The recovered product was washed with isopropanol and dried under reduced pressure to obtain 6 g of the hydrochloride of the said indole melting at 260° C. The product was crystallized from ethanol for analysis.

Analysis: $C_{16}H_{21}ClN_2$; molecular weight=276.821
Calculated: %C 69.42, %H 7.65, %Cl 12.81, %N 10.12.
Found: %C 69.2, %H 7.9, %Cl 12.7, %N 10.1.

EXAMPLE 6

6-methoxy-3-(1-propyl-1,2,3,6-tetrahydropyridin-4-yl)-1H-indole hydrochloride

Step A:
6-methoxy-3-(1,2,3,6-tetrahydropyridin-4-yl)-1H-indole

A mixture of 20 g of 6-methoxy-1H-indole, 41.75 g of the hydrochloride of 4-piperidone monohydrate and 205 ml of methanolic 2 N potassium hydroxide was refluxed for 8½ hours and was then stirred overnight at room temperature. The mixture was slowly diluted with water to a volume of 1.2 liters and crystallization was effected. The mixture was stirred for 30 minutes and was filtered and the recovered product was carefully rinsed with water and dried to obtain 23.05 g of 6-methoxy-3-(1,2,3,6-tetrahydropyridin-4-yl)-1H-indole melting at 193°–194° C.

Step B:
6-methoxy-3-(1-propyl-1,2,3,6-tetrahydropyridin-4-yl)-1H-indole hydrochloride A mixture of 10 g of the product of Step A, 200 ml of dimethylformamide, 9.28 g of sodium carbonate and 8.93 g of propyl iodide was stirred under an inert atmosphere for 5 hours and was then poured into 1.5 liters of water. The mixture was allowed to crystallize and was stirred for one hour and then vacuum filtered. The recovered product was rinsed with water and dried at 50° C. under reduced pressure in the presence of a dehydrating agent to obtain 9.9 g of 6-methoxy-3-(1-propyl-1,2,3,6-tetrahydropyridin-4-yl)-1H-indole melting at 219°–220° C.

7.3 g of the said product were suspended in 105 ml of cooled ethanol and 7.5 ml of an ethanol solution saturated with gaseous hydrogen chloride were added thereto until the pH was acidic. The mixture was stirred for 90 minutes at 0° to 5° C. and was vacuum filtered. The recovered product was washed with ethanol and dried at 50° C. under reduced pressure to obtain 8.25 g of raw product which was crystallized from water to obtain 6.2 g of the hydrochloride of the said indole melting at 260° C.

Analysis: $C_{17}H_{23}ClN_2O$; molecular weight=306.843
Calculated: %C 66.54, %H 7.55, %Cl 11.55, %N 9.12.
Found: %C 66.2, %H 7.7, %Cl 11.7, %N 9.0.

EXAMPLE 7

3-[1-(2-phenethyl)-1,2,3,6-tetrahydropyridin-4-yl]-1H-indole hydrochloride

A mixture of 6.94 g of 3-(1,2,3,6-tetrahydropyridin-4-yl)-1H-indole, 105 ml of dimethylformamide, 7.42 g of sodium carbonate and 5.95 ml of phenethyl bromide was stirred for 5 hours at 45° C. and was then poured into a stirred one liter of ice water after which crystallization occured. The mixture was stirred for 2 hours and then filtered and the recovered product was rinsed with water and dried overnight under reduced pressure in the presence of a dehydrating agent to obtain 10.23 g of a yellow product melting at 203° C. The latter was crystallized from ethanol to obtain 7.33 g of 3-[1-(2-phenethyl)-1,2,3,6-tetrahydropyridin-4-yl]-1H-indole melting at 206° to 207° C.

A suspension of 8.24 g of the said product in 85 ml of iced ethanol was admixed with stirring with an ethanol solution of hydrogen chloride until the pH was acidic and the mixture was stirred for one hour and was filtered. The recovered product was rinsed with ethanol and was twice crystallized from methanol to obtain 6.99 g of pure hydrochloride of the said indole melting at 280° C.

Analysis: $C_{21}H_{23}N_2Cl$; molecular weight=338.888
Calculated: %C 74.42, %H 6.84, %Cl 8.26, %N 10.46.
Found: %C 74.4, %H 6.9, %Cl 7.9, %N 10.7.

EXAMPLE 8

3-[1-(2-propenyl)-1,2,3,6-tetrahydropyridin-4-yl]-1H-indole hydrochloride

A mixture of 13.86 g of 3-(1,2,3,6-tetrahydropyridin-4-yl)-1H-indole, 210 ml of dimethylformamide, 14.84 g of sodium carbonate and 7.3 ml of redistilled allyl bromide was stirred under an inert atmosphere for one hour at 32° C. and was then poured into 2 liters of water which caused precipitation. The mixture was stirred for one hour and was filtered and the recovered product was rinsed and was dried under reduced pressure in the presence of a dehydrating agent to obtain 16.61 g of a pale yellow product melting at 177°–179° C. The product was crystallized 3 times from ethyl acetate to obtain 9.72 g of 3-[1-(2-propenyl)-1,2,3,6-tetrahydropyridin-4-yl]-1H-indole melting at 177°–179° C.

A suspension of the said product in 85 ml of iced ethanol was acidified with an ethanol solution of gaseous hydrogen chloride and the mixture was stirred at 5° C. for one hour and was filtered. The product was rinsed with ethanol and was dried at 50° C. under reduced pressure to obtain 9.36 g of product which was crystallized from ethanol to obtain 7.45 g of pure hydrochloride of the said indole melting at 177°–178° C. and 217°–218° C.

Analysis: $C_{16}H_{19}N_2Cl$; molecular weight=274.8 Calculated: %C 69.93, %H 6.96, %N 10.19, %Cl 12.90.
Found: %C 69.7, %H 7.1, %N 9.9, %Cl 13.0.

EXAMPLE 9

5-chloro-3-(1-propyl-1,2,3,6-tetrahydropyridin-4-yl)-1H-indole hydrochloride

A mixture of 9.28 g of 5-chloro-3-(1,2,3,6-tetrahydropyridin-4-yl)-1H-indole (prepared by the process of Belgium Pat. No. 858,101), 140 ml of dimethylformamide, 8.48 g of sodium carbonate and 4.67 g of propyl iodide was stirred for 5 hours at room temperature under an inert atmosphere and was then poured with stirring into 1.4 liters of water after which crystallization occured. The mixture was filtered and the recovered product was rinsed with water and dried under reduced pressure in the presence of a dehydrating agent. The product was crystallized from ethanol to obtain 6.95 g of 5-chloro-3-(1-propyl-1,2,3,6-tetrahydropyridin-4-yl)-1H-indole hydrochloride melting at 229°–230° C.

A suspension of the said product in 105 ml of iced ethanol was admixed with a saturated ethanolic hydrogen chloride solution until the pH was acidic and the mixture was stirred for 2½ hours at 0° C. and was filtered. The recovered product was rinsed with ethanol and was dried in an oven to obtain 7.566 g of raw product which was crystallized from ethanol to obtain 5.047 g of the hydrochloride of the said indole in the form of clear yellow crystals melting at 260° C.

Analysis: $C_{16}H_{20}Cl_2N_2$; molecular weight=311.256
Calculated: %C 61.74, %H 6.47, %Cl 22.78, %N 8.99.
Found: %C 61.6, %H 6.5, %Cl 22.7, %N 8.8.

EXAMPLE 10

5-chloro-3-(1-ethyl-1,2,3,6-tetrahydropyridin-4-yl)-1H-indole hydrochloride

A mixture of 12 g of 5-chloro-3-(1,2,3,6-tetrahydropyridin-4-yl)-1H-indole, 120 ml of anhydrous dimethylformamide, 10.92 g of sodium carbonate and 5.1 ml of bromoethane was stirred under an inert atmosphere at room temperature for 6½ hours and then 350 ml of distilled water was slowly added thereto which caused precipitation. The mixture was stirred for 90 minutes and after standing overnight, was vacuum filtered. The recovered product was empasted 3 times with water and once with 50% aqueous ethanol and was dried in the presence of a dehydrating agent to obtain 9.48 g of yellow product melting at 208°–210° C. which was crystallized twice from ethanol to obtain 7.487 g of 5-chloro-3-(1-ethyl-1,2,3,6-tetrahydropyridin-4-yl)-1H-indole.

A suspension of the said product in 40 ml of ethanol cooled to 0° C. was adjusted to a pH of 1 by addition of an ethanol solution of hydrogen chloride and the mixture was stirred for 30 minutes at 0° C. The mixture stood for one hour at 0° C. and was then filtered. The recovered product was rinsed with iced ethanol and was dried at 50° C. under reduced pressure to obtain 7.3 g of product melting at 225° C. which was crystallized from iced ethanol to obtain 5.9 g of the hydrochloride of the said indole melting at 225° C.

Analysis: $C_{15}H_{18}Cl_2N_2$; molecular weight=297.239
Calculated: %C 60.61, %H 6.1, %N 9.42, %Cl 23.85.
Found: %C 60.4, %H 6.1, %N 9.3, %Cl 23.6.

EXAMPLE 11

5-chloro-3-[1-cyclopropylmethyl-1,2,3,6-tetrahydropyridin-4-yl]-1H-indole hydrochloride A mixture of 12.5 g of 5-chloro-3-(1,2,3,6-tetrahydropyridin-4-yl)-1H-indole, 120 ml of anhydrous dimethylformamide, 11.5 g of sodium carbonate and 6.5 ml of cyclopropylmethyl chloride was stirred for 24 hours under an inert atmosphere at 70° C. and was then cooled to 30° C. after which 300 ml of distilled water were added thereto while cooling in an ice bath. Precipitation occured and the mixture was stirred for 45 minutes, stood for 15 minutes and was then filtered. The product was washed 3 times with distilled water and was empasted with 20 ml of 50% aqueous ethanol. The product was dried at 50° C. under reduced pressure in the presence of a dehydrating agent to obtain 13.54 g of raw product which was dissolved in 350 ml of refluxing ethanol. The solution was filtered and the filtrate was concentrated to 300 ml for crystallization. The solution was cooled to room temperature and was held in a refrigerator for 90 minutes. The mixture was vacuum filtered and the product was rinsed with ethanol and dried under reduced pressure to obtain 7.8 g of 5-chloro-3-(1-cyclopropylmethyl-1,2,3,6-tetrahydropyridin-4-yl)-1H-indole melting at 205° C.

A suspension of the said product in 80 ml of ethanol cooled in an ice bath was adjusted to a pH of 1 by addition of ethanolic hydrogen chloride and the mixture was stirred for one hour during which a cream precipitate formed. The mixture stood for 15 minutes and was vacuum filtered and the product was rinsed with ethanol, dried under reduced pressure and was crystallized from ethanol to obtain 6.9 g of the hydrochloride of the said indole melting at 242°–244° C.

Analysis: $C_{17}H_{20}Cl_2N_2$; molecular weight=323.268
Calculated: %C 63.16, %H 6.23, %Cl 21.93, %N 8.66.
Found: %C 63.3, %H 6.2, %Cl 22.2, %N 8.6.

EXAMPLE 12

2-methyl-6-methoxy-3-(1-propyl-1,2,3,6-tetrahydropyridin-4-yl)-1H-indole hydrochloride

STEP A:
6-methoxy-2-methyl-3-(1,2,3,6-tetrahydropyridin-4-yl)-1H-indole hydrochloride A mixture of 2 g of 2-methyl-6-methoxy-1H-indole, 4 g of the hydrochloride of 4-piperidone monohydrate and 40 ml of acetic acid was stirred at 100° C. under an inert atmosphere for 90 minutes and the mixture was cooled and poured into a solution of 150 g of ice and 80 ml of 22° Be ammonium hydroxide. The mixture was extracted with ethyl acetate and the organic phase was washed with water, dried over magnesium sulfate and evaporated to dryness and reduced pressure. The residue was empasted with hot ethyl acetate and the mixture was cooled and vacuum filtered. The product was washed with ethyl acetate and dried under reduced pressure to obtain 2.5 g of raw product which was dissolved in 50 ml of hot isopropanol. The solution was cooled and made acidic by dropwise addition of an isopropanol solution of gaseous hydrogen chloride. The mixture stood overnight after crystallization was induced and was vacuum filtered. The product was washed with isopropanol and was dried under reduced pressure to obtain 2.25 of 2-methyl-6-methoxy-3-(1,2,3,6-tetrahydropyridin-4-yl)-1H-indole hydrochloride melting at 270° C.

Analysis: $C_{15}H_{19}ClN_2O$ Calculated: %C 64.52, %H 6.87, %Cl 12.72, %N 10.05. Found: %C 64.5, %H 7.0, %Cl 13.0, %N 9.9.

STEP B:
2-methyl-6-methoxy-3-(1-propyl-1,2,3,6-tetrahydropyridin-4-yl)-1H-indole hydrochloride A mixture of 10.3 g of the product of Step A, 11.845 g of sodium carbonate, 103 ml of dimethylformamide and 4.82 ml of propyl iodide was stirred under an nitrogen atmosphere at 40° C. for 4½ hours and was then poured with stirring into water. The resulting gum was extracted with ethyl acetate and the organic phase was washed with water, with aqueous sodium chloride solution, dried and evaporated to dryness. The 10.1 g of resin were empasted with 50 ml of ethanol during which crystallization occurred and the mixture was stirred at room temperature for 45 minutes. The mixture was iced with stirring for 30 minutes, allowed to stand for 30 minutes and was then vacuum filtered. The product was rinsed with ethanol and then with ether to obtain 7.8 g of 2-methyl-6-methoxy-3-(1-propyl-1,2,3,6-tetrahydropyridin-4-yl)-1H-indole melting at 90°–95° C.

A solution of 9.1 g of the said product in 70 ml of isopropanol was filtered, iced and adjusted to an acid pH by addition of isopropanol saturated with gaseous hydrogen chloride after which precipitation occurred. The mixture was stirred for 30 minutes, stood for 30 minutes and was vacuum filtered at room temperature. The product was rinsed with isopropanol to obtain 8.73 g of a product melting at 260° C. which was crystallized from methanol to obtain 4.4 g of the hydrochloride of the said indole melting at 275° C.

Analysis: $C_{18}H_{25}ClN_2O$; molecular weight=320.87
Calculated: %C 67.37, %H 7.85, %Cl 11.05, %N 8.73.
Found: %C 67.2, %H 8.00, %Cl 11, %N 8.6.

EXAMPLE 13

Tablets were prepared containing 10 mg of 3-(1-propyl-1,2,3,6-tetrahydropyridin-4-yl)-1H-indole hydrochloride or 25 mg of 3-(1-ethyl-1,2,3,6-tetrahydropyridin-4-yl)-1H-indole hydrochloride or 25 mg of 5-chloro-3-(1-propyl-1,2,3,6-tetrahydropyridin-4-yl)-1H-indole hydrochloride and sufficient excipient of lactose, starch, talc and magnesium stearate for a final weight of 200 mg.

PHARMACOLOGICAL DATA

A. Potentialization of amphetamine stereotypies

The tests were effected on groups of 5 male rats weighing 150 to 180 g with the animals individually placed in a grilled cage (29×25×17 cm) containing a few scraps of wood chips. A delay of one hour was observed between the intraperitoneal administration of the test compound and the intraperitoneal injection of 5 mg/kg of dexamphetamine sulfate and the behavior of the animals was noted every half hour for 5 hours with the preconceived readings of Halliwell et al [Brit. J. Pharmacol., Vol. 23 (1964), p 330-350] as follows: The animal was asleep (0), the animal was awake but immobile (1), the animal was turning in the cage (2), the animal was sniffing the cover (3), the animal was licking the sides (4), the animal was touching the scraps of wood chips or bars of the cage with his teeth (5), and the animal was gnawing on the bars of the cage or the scraps of wood chips (6).

The intensity of the stereotypies were expressed in a form of a score of 0 to 30 corresponding to the total of the values obtained for each group of 5 rats. The sum of the scores totaled in 5 hours was calculated. The dose of the test compound which augmented by about 100% the sum of the scores in 5 hours was 5 mg/kg for the product of Example 1 and 10 mg/kg for the product of Example 2.

B. Antagonism to apomorphine stereotypies

The test was inspired by Janssen et al/Arzneim. Forsch, Vol. 15 (1965), p. 104–117; Vol. 17 (1967), p. 841–854/with group of 5 rats with each rat being individually placed in a plexiglass box (20×10×10 cm; Nicolet) with the bottom covered with a thin layer of wood chips. A dose of 1.5 mg/kg of apomorphine hydrochloride was intravenously administered 30 minutes after intraperitoneal administration of the test product. The animals were observed every minute for 15 minutes after the apomorphine injection and the stereotypie movements of the oral sphere were evaluated by the method of Boissier et al/Therapie., Vol. 25, (1970), p. 933-949/as follows: no characteristic reaction (0), a few sniffles, lickings and chewings (1), intense sniffles and continous lickings (2) and continous chewings (3). The intensity of the stereotypies were expressed in a form of a score of 0 to 15 corresponding to the total of the values obtained for each group of 5 rats, 15 minutes after the apomorphine injection. The dose which reduced by 50% the total of the scores was 10 to 20 mg/kg for the compounds of Examples 1, 2, and 3, 25 mg/kg for the compound of Example 8 and 3 mg/kg for the compound of Example 9.

C. Potentialization of yohimbine toxicity

The test used was that of Quinton /Brit. J. Pharmacol., Vol. 21 (1963) p. 51/ in which a sublethal dose of 30 mg/kg of yohimbine hydrochloride was intraperitoneally injected to groups of 10 male mice weighing 22 to 24 g. The test compound was intraperitoneally administered 1 hour before the yohimbine injection and the number of dead mice was determined 24 hours after the yohimbine injection. The product of Example 2 potentialized the toxicity of the yohimbine at a dose of 15 mg/kg.

D. Antagonism towards catalepsy caused by prochlorpemazine

The test was effected on groups of 5 male rats weighing about 100 g and the test compound was administered intraperitoneally simultaneously with the intraperitoneal administration of 15 mg/kg of prochlorpemazine. The catalepsy was observed every hour for 7 hours following the test of crossing of homolateral paws [Boissier et al., Therapie, Vol. 18 (1963), p. 1257–1277] with the following notations: The animal refused to cross the front paws with the homolateral rear paws (0), the animal accepted the crossing only for one side (0.5) and the animal accepted the crossing of both sides (1). The compound of Example 1 opposed catalepsy induced by prochlorpemazine at a dose below 5 mg/kg while the compounds of Examples 2,5 and 7 were effective at a dose below 10 mg/kg.

E. Antiemetic activity

The antagonism to vomitting provoked by apomorphine was studied in dogs [Chen et al., J. Pharmac. Exp. Therap., Vol. 93 (1959), p. 245–250] and the number of vomits provoked by subcutaneous injection of 0.1 mg/kg of apomorphine hydrochloride was determined for each animal 8 days before the test. The test compound in aqueous solution was subcutaneously administered at varying doses one half hour before the apomorphine hydrochloride. The compound of Example 1 was antagonistic to the provoked vomits by reducing the same by 50% at 0.5 mg/kg, the compound of Example 2 was effective at 0.045 mg/kg and the compound of Example 9 was effective at 0.008 mg/kg.

F. Acute toxicity

The acute toxicity was determined on groups of 10 mice weighing about 20 g and the test compounds were intraperitoneally administered at increasing doses. The mortality was determined 48 hours after the administration and the $LD_{50}$ dose for the compound of Example 1 was greater than 400 mg/kg and for the product of Example 2 was greater than 100 mg kg and for the compounds of Examples 4 and 9 was 150 mg/kg, for Examples 6 and 8 was 200 mg/kg and for Example 7 was greater than 600 mg/kg.

Various modifications of the products and processes of the invention may be made without departing from the spirit or scope thereof and it is to be understood that the invention is intended to be limited only as defined in the appended claims.

We claim:

1. A compound selected from the group consisting of compounds of the formula

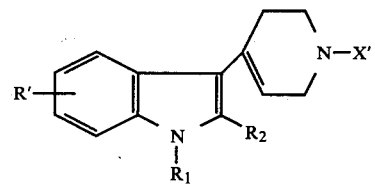

wherein R' is selected from the group consisting of hydrogen, halogen and alkoxy of 1 to 3 carbon atoms, $R_1$ and $R_2$ are individually selected from the group consisting of hydrogen and alkyl of 1 to 3 carbon atoms and X' is selected from the group consisting of alkyl of 1 to 6 carbon atoms, cycloalkyl of 4 to 7 carbon atoms, alkenyl and alkynyl of 2 to 5 carbon atoms and aralkyl of 7 to 12 carbon atoms with the proviso that when X' is methyl, at least one of R', $R_1$ and $R_2$ contain more than one carbon atom and when X' is benzyl, at least one of R', $R_1$ and $R_2$ must not be hydrogen and their non-toxic, pharmaceutically acceptable acid addition salts.

2. A compound of claim 1 wherein R' is selected from the group consisting of hydrogen and alkoxy of 1 to 3 carbon atoms and X' is alkyl of 1 to 6 carbon atoms with the proviso that when X' is methyl, at least one of R', $R_1$ and $R_2$ contain more than one carbon atom.

3. A compound of claim 1 wherein R' is halogen, $R_1$ and $R_2$ are individually hydrogen or methyl and X' is alkyl of 2 to 6 carbon atoms.

4. A compound of claim 1 wherein R' is 5-chloro, $R_1$ and $R_2$ are hydrogen and X' is alkyl of 2 to 6 carbon atoms.

5. A compound of claim 2 wherein R' is hydrogen or methoxy, $R_1$ and $R_2$ are individually hydrogen or methyl and X' is alkyl of 2 to 6 carbon atoms.

6. A compound of claim 2 wherein R' is hydrogen or 5-methoxy, $R_1$ and $R_2$ are hydrogen and X' is alkyl of 2 to 6 carbon atoms.

7. A compound of claim 2 which is the neutral fumarate of 5-methoxy-3-(1-propyl-1,2,3,6-tetrahydropyridin-4-yl)-1H-indole.

8. A compound of claim 2 which is the 3-(1-propyl-1,2,3,6-tetrahydropyridin-4-yl)-1H-indole hydrochloride.

9. A compound of claim 2 which is the 3-(1-pentyl-1,2,3,6-tetrahydropyridin-4-yl)-1H-indole hydrochloride.

10. A compound of claim 1 which is the 5-chloro-3-(1-propyl-1,2,3,6-tetrahydropyridin-4-yl)-1H-indole hydrochloride.

11. A compound of claim 1 which is the 3-(1-ethyl-1,2,3,6-tetrahydropyridin-4-yl)-1H-indole hydrochloride.

12. A compound of claim 1 which is the 3-(1-isopropyl-1,2,3,6-tetrahydropyridin-4-yl)-1H-indole hydrochloride.

13. A compound of claim 1 which is the 6-methoxy-3-(1-propyl-1,2,3,6-tetrahydropyridin-4-yl)-1H-indole hydrochloride.

14. An antidepressive, neuroleptic and antiemetic composition comprising an antidepressantly, neuroleptically and antiemetically effective amount of at least one compound of claim 1 and an inert pharmaceutical carrier.

15. A composition of claim 14 wherein R' is selected from the group consisting of hydrogen and alkoxy of 1 to 3 carbon atoms and X' is alkyl of 1 to 6 carbon atoms with the proviso that when X' is methyl, at least one of R', $R_1$ and $R_2$ contain more than one carbon atom.

16. A composition of claim 14 wherein R' is halogen, $R_1$ and $R_2$ are individually hydrogen or methyl and X' is alkyl of 2 to 6 carbon atoms.

17. A composition of claim 14 wherein R' is 5-chloro, $R_1$ and $R_2$ are hydrogen and X' is alkyl of 2 to 6 carbon atoms.

18. A composition of claim 14 wherein R' is hydrogen or methoxy, $R_1$ and $R_2$ are individually hydrogen or methyl and X' is alkyl of 2 to 6 carbon atoms.

19. A composition of claim 14 wherein R' is hydrogen or 5-methoxy, $R_1$ and $R_2$ are hydrogen and X' is alkyl of 2 to 6 carbon atoms.

20. A composition of claim 14 wherein the compound is the neutral fumarate of 5-methoxy-3-(1-propyl-1,2,3,6-tetrahydropyridin-4-yl)-1H-indole.

21. A composition of claim 14 wherein the compound is 3-(1-propyl-1,2,3,6-tetrahydropyridin-4-yl)-1H-indole hydrochloride.

22. A composition of claim 14 wherein the compound is 3-(1-pentyl-1,2,3,6-tetrahydropyridin-4-yl)-1H-indole hydrochloride.

23. A composition of claim 14 wherein the compound is 5-chloro-3-(1-propyl-1,2,3,6-tetrahydropyridin-4-yl)-1H-indole hydrochloride.

24. A composition of claim 14 wherein the compound is 3-(1-ethyl-1,2,3,6-tetrahydropyridin-4-yl)-1H-indole hydrochloride.

25. A composition of claim 14 wherein the compound is 3-(1-isopropyl-1,2,3,6-tetrahydropyridin-4-yl)-1H-indole hydrochloride.

26. A composition of claim 14 wherein the compound is 6-methoxy-3-(1-propyl-1,2,3,6-tetrahydropyridin-4-yl)-1H-indole hydrochloride.

27. A method of treating psychic disorders in warm-blooded animals comprising administering to warm-blooded animals an amount of at least one compound of claim 1 sufficient to relieve psychic disorders.

28. A method of claim 27 wherein R' is selected from the group consisting of hydrogen and alkoxy of 1 to 3 carbon atoms and X' is alkyl of 1 to 6 carbon atoms with the proviso that when X' is methyl, at least one of R', $R_1$ and $R_2$ contain more than one carbon atom.

29. A method of claim 27 wherein R' is halogen, $R_1$ and $R_2$ are individually hydrogen or methyl and X' is alkyl of 2 to 6 carbon atoms.

30. A method of claim 27 wherein R' is 5-chloro, $R_1$ and $R_2$ are hydrogen and X' is alkyl of 2 to 6 carbon atoms.

31. A method of claim 27 wherein R' is hydrogen or methoxy, $R_1$ and $R_2$ are individually hydrogen or methyl and X' is alkyl of 2 to 6 carbon atoms.

32. A method of claim 27 wherein R' is hydrogen or 5-methoxy, $R_1$ and $R_2$ are hydrogen and X' is alkyl of 2 to 6 carbon atoms.

33. A method of claim 27 wherein the compound is the neutral fumarate of 5-methoxy-3-(1-propyl-1,2,3,6-tetrahydropyridin-4-yl)-1H-indole.

34. A method of claim 27 wherein the compound is 3-(1-propyl-1,2,3,6-tetrahydropyridin-4-yl)-1H-indole hydrochloride.

35. A method of claim 27 wherein the compound is 3-(1-pentyl-1,2,3,6-tetrahydropyridin-4-yl)-1H-indole hydrochloride.

36. A method of claim 27 wherein the compound is 5-chloro-3-(1-propyl-1,2,3,6-tetrahydropyridin-4-yl)-1H-indole hydrochloride.

37. A method of claim 27 wherein the compound is 3-(1-ethyl-1,2,3,6-tetrahydropyridin-4-yl)-1H-indole hydrochloride.

38. A method of claim 27 wherein the compound is 3-(1-isopropyl-1,2,3,6-tetrahydropyridin-4-yl)-1H-indole hydrochloride.

39. A method of claim 27 wherein the compound is 6-methoxy-3-(1-propyl-1,2,3,6-tetrahydropyridin-4-yl)-1H-indole hydrochloride.

* * * * *